United States Patent
Warntjes

(10) Patent No.: US 9,993,156 B2
(45) Date of Patent: Jun. 12, 2018

(54) METHODS AND APPARATUSES FOR RELATING MULTIPLE MAGNETIC RESONANCE PHYSICAL PARAMETERS TO MYELIN CONTENT IN THE BRAIN

(75) Inventor: Marcel Warntjes, Ljungsbro (SE)

(73) Assignee: SyntheticMR AB, Linkoping (SE)

( * ) Notice: Subject to any disclaimer, the term of this patent is extended or adjusted under 35 U.S.C. 154(b) by 0 days. days.

(21) Appl. No.: 13/879,321

(22) PCT Filed: Oct. 14, 2010

(86) PCT No.: PCT/SE2010/000245
§ 371 (c)(1),
(2), (4) Date: May 27, 2013

(87) PCT Pub. No.: WO2012/050487
PCT Pub. Date: Apr. 19, 2012

(65) Prior Publication Data
US 2014/0180061 A1     Jun. 26, 2014

(51) Int. Cl.
A61B 5/00 (2006.01)
G01R 33/50 (2006.01)
G01R 33/56 (2006.01)
A61B 5/055 (2006.01)

(52) U.S. Cl.
CPC .......... *A61B 5/0042* (2013.01); *A61B 5/055* (2013.01); *G01R 33/50* (2013.01); *G01R 33/5608* (2013.01)

(58) Field of Classification Search
CPC .................................................. A61B 5/055
See application file for complete search history.

(56) References Cited

U.S. PATENT DOCUMENTS

| | | | |
|---|---|---|---|
| 4,634,979 A | 1/1987 | Riederer et al. | |
| 4,641,095 A | 2/1987 | Riederer | |
| 4,881,033 A | 11/1989 | Denison et al. | |
| 5,262,945 A | 11/1993 | DeCarli et al. | |
| 5,486,763 A | 1/1996 | Alfano | |
| 6,366,797 B1 | 4/2002 | Fisher et al. | |
| 6,823,205 B1 | 11/2004 | Jara | |
| 6,917,199 B2 | 7/2005 | Jara | |
| 7,002,345 B2 | 2/2006 | Jara | |
| 7,973,530 B2 | 7/2011 | Warntjes | |
| 2003/0139659 A1* | 7/2003 | Dale et al. | 600/407 |

(Continued)

FOREIGN PATENT DOCUMENTS

WO    WO 2007079207 A2 *  7/2007

OTHER PUBLICATIONS

Levesque, I. R., Pike, G. B., "Characterizing Healthy and Diseased WHite Matter Using Quantitative Magnetization Transfer and Multicomponent T2 Relaxometry: A Unified View via a FOur-Pool Model", Magnetic Resonance in Medicine, 62:1487-1496, 2009.*

(Continued)

*Primary Examiner* — Rochelle Turchen
*Assistant Examiner* — Joanne Hoffman
(74) *Attorney, Agent, or Firm* — Oblon, McClelland, Maier & Neustadt, L.L.P.

(57) ABSTRACT

A computerized method of generating a map of myelin tissue of a brain is described. In addition sub-maps of different myelin contents can be imaged. The method uses a simulation model comprising at least two interacting tissue compartments.

19 Claims, 6 Drawing Sheets

(56) References Cited

U.S. PATENT DOCUMENTS

| | | | |
|---|---|---|---|
| 2005/0190955 A1* | 9/2005 | Brown .................. | G01R 33/56 |
| | | | 382/128 |
| 2007/0053554 A1* | 3/2007 | Fayad et al. .................. | 382/128 |
| 2007/0167727 A1 | 7/2007 | Menezes et al. | |
| 2008/0292194 A1 | 11/2008 | Schmidt | |
| 2009/0267945 A1 | 10/2009 | Warntjes | |
| 2009/0312625 A1* | 12/2009 | Du .............................. | 600/410 |
| 2010/0103166 A1 | 4/2010 | Warntjes | |
| 2010/0127704 A1* | 5/2010 | Warntjes ...................... | 324/309 |
| 2010/0166284 A1 | 7/2010 | Smith et al. | |
| 2010/0260396 A1* | 10/2010 | Brandt ................. | G06K 9/4671 |
| | | | 382/131 |
| 2011/0018537 A1 | 1/2011 | Warntjes | |

OTHER PUBLICATIONS

Stanisz, G. J., Odrobina, E. E., Pun, J., Escaravage, M., Graham, S. J., Bronskill, M. J., and Henkelman, R. M., "T1, T2 Relaxation and Magnetization Transfer in Tissue at 3T", Magnetic Resonance in Medicin, 54:507-512, 2005.*

Ives, "Characterizing Healthy and Diseased White Matter Using Quantitative Magnetization Transfer and Multicomponent T2 Relaxometry: A Unified View via a Four-Pool Model", Magnetic Resonance in Medicine, 62: 1487-1496 (2009).*

Arhelger, "Rapid Simultaneous Mapping of Total and Myelin Water Content, T1 and T2 in Multiple Sclerosis", Medical Physics, Cornell Library, pp. 1-27, 2010.*

I.R. Levesque and G.B. Pike, Characterizing White Matter Pathology with Quantitative Magnetization Transfer Imaging: Insight from a Four-Pool Model, Proc. Int'l Soc. Mag. Reson. Med., Apr. 18, 2009, p. 182, vol. 17.

Japan Patent Office, Office Action in App. No. 2013-533815, dated May 20, 2014.

R. Maitra et al., Bayesian Reconstruction in Synthetic Magnetic Resonance Imaging, Proc. SPIE, 1998, pp. 39-47, vol. 3459.

M. Prastawa et al., Synthetic Ground Truth for Validation of Brain Tumor MRI Segmentation, Med Image Comput Comput Assist Interv., 2005, pp. 26-33, 8 (Pt 1).

K.H. Cheng et al., In-vivo Tissue Characterization of Brain by Synthetic MR Proton Relaxation and Statistical Chisquares Parameter Maps, Proc. 8th Symposium on Computer-Based Medical Systems, 1995, pp. 338-345, IEEE.

M. Warntjes et al., Rapid Magnetic Resonance Quantification on the Brain: Optimization for Clinical Usage, Magnetic Resonance in Medicine, 2008, pp. 320-329, vol. 60, Wiley-Liss, Inc.

B. Grassiot et al., Quantification and Clinical Relevance of Brain Atrophy in Multiple Sclerosis: A Review, J. Neurol., 2009, pp. 1397-1412, vol. 256, Springer.

J. West et al., Novel Whole Brain Segmentation and Volume Estimation Using Quantitative MRI, Eur. Radiol., Nov. 24, 2011, pp. 1-10, Springer.

Sweden Patent Office, Int'l Search Report in PCT/SE2010/000245, dated Jun. 23, 2011.

Extended European Search Report dated Dec. 15, 2017 in European Patent Application No. 10858465.7.

Sean C.L. Deoni, et al., "Gleaning Multicomponent $T_1$ and $T_2$ Information From Steady-State Imaging Data" Magnetic Resonance in Medicine, vol. 60, No. 6, Dec. 1, 2008, pp. 1372-1387, XP055317994.

Cornelia Laule, et al., "Magnetic Resonance Imaging of Myelin" Neurotherapeutics: The Journal of the American Society for Experimental NeuroTherapeutics, vol. 4, No. 3, Jun. 25, 2007 and Jul. 2007, pp. 460-484, XP022127925.

Cornelia Laule, et al., "Myelin water imaging of multiple sclerosis at 7 T: Correlations with histopathology", NeuroImage, vol. 40, No. 4, May 1, 2008, pp. 1575-1580, XP023176185.

Alex MacKay, et al., "Insights into brain microstructure from the $T_2$ distribution" Magnetic Resonance Imaging, vol. 24, No. 4, May 1, 2006, pp. 515-525, XP028004852.

Alex MacKay, et al., "In Vivo Visualization of Myelin Water in Brain by Magnetic Resonance" Magnetic Resonance in Medicine, vol. 32, No. 6, Jun. 1, 1994, pp. 673-677, XP000444472.

\* cited by examiner

METHODS AND APPARATUSES FOR RELATING MULTIPLE MAGNETIC RESONANCE PHYSICAL PARAMETERS TO MYELIN CONTENT IN THE BRAIN

TECHNICAL FIELD

The present invention relates to a method, system and computer program product for generating fractional maps of brain tissue retrieved by a Magnetic Resonance (MR) quantification sequence. In particular a method, system and computer program product for generating a myelin fraction map of the brain based on multiple physical parameters can be provided using the invention.

BACKGROUND

Magnetic Resonance Imaging (MRI) can generate cross-sectional images in any plane (including oblique planes). Medical MRI most frequently relies on the relaxation properties of excited hydrogen nuclei (protons) in water and fat. When the object to be imaged is placed in a powerful, uniform magnetic field the spins of the atomic nuclei with non-integer spin numbers within the tissue all align either parallel to the magnetic field or anti-parallel. The output result of an MRI scan is an MRI contrast image or a series of MRI contrast images.

In order to understand MRI contrast, it is important to have some understanding of the time constants involved in relaxation processes that establish equilibrium following RF excitation. As the excited protons relax and realign, they emit energy at rates which are recorded to provide information about their environment. The realignment of proton spins with the magnetic field is termed longitudinal relaxation and the time (typically about 1 sec) required for a certain percentage of the tissue nuclei to realign is termed "Time 1" or T1. T2-weighted imaging relies upon local dephasing of spins following the application of the transverse energy pulse; the transverse relaxation time (typically <100 ms for tissue) is termed "Time 2" or T2. These relaxation times are also expressed as relaxation rates R1 (=1/T1) and R2 (=1/T2). The total signal depends on the number of protons, or proton density PD. On the scanner console all available parameters, such as echo time TE, repetition time TR, flip angle α and the application of preparation pulses (and many more), are set to certain values. Each specific set of parameters generates a particular signal intensity in the resulting images depending on the characteristics of the measured tissue.

In conventional contrast imaging the absolute signal intensity observed in the images has no direct meaning; it is rather the intensity difference, the contrast, between different tissues that lead to a diagnosis. A more quantitative approach can be applied based on the measurement of physical parameters such as R1, R2 and PD. These values are independent of scanner settings and hence reflect the underlying tissue.

A Bloch simulation model (see e.g. Levesque R, Pike G B. Characterizing healthy and diseased white matter using quantitative magnetization transfer and multicomponent T2 relaxometry: A unified view via a four-pool model. Mag Reson Med 2009; 62:1487-1496) can be set up to relate tissue composition to the expected observation of MR quantification results in a direct measurement of the included tissues, which could lead to MR computer aided diagnose.

One type of brain tissue of particular interest is called Myelin. Myelin is particularly interesting since it forms the insulating sheaths around the nerve axons in the brain. Degradation or damage to myelin may lead to a range of diseases such as dementia and multiple sclerosis. It can also be an important factor to determine the extent of edema, stroke or brain tumors. Myelin consists of thin layers of fatty tissue (semi-solids) and water.

There is a constant need to improve diagnostic and imaging methods relating to MRI. In particular methods and apparatuses for improved imaging and analysis of brain tissue such as myelin is desired.

SUMMARY

It is an object of the present invention to provide a method and device for relating the measurement of multiple physical parameters (e.g. the combination of T1 and T2 relaxation times, R1 and R2 relaxation rates and proton density PD, or a subset thereof) to tissue content of the brain.

This object and others are obtained by the method and device as set out in the appended claims.

A tissue of particular interest in MR imaging is myelin. In accordance with embodiments of the invention methods, apparatuses and computer programs for deriving a myelin fraction from measurement of multiple physical parameters (e.g. the combination of T1 and T2 relaxation times, R1 and R2 relaxation rates and proton density PD, or a subset thereof) are provided. The multiple physical parameters can be derived from a sequence of MR images. Also the myelin water, the myelin semi-solids, the intra- and extracellular (interstitial) water, the non-myelin semi-solids, the free water, the total water content, the myelin water fraction, edema, the total myelin content of the brain and the relative myelin fraction of the brain can be obtained and provided as output.

In accordance with one embodiment a computerized method of generating a map of myelin tissue of a brain is provided. The method comprises generating maps of two or more physical properties of the brain. The method also comprises forming a simulation model comprising at least two interacting tissue compartments and generating physical properties using the simulation model as input. The method then generates a myelin fraction map by relating observed physical properties of the generated maps to the physical properties generated using the simulation model, and using the relationship for generating the myelin fraction map.

In accordance with one embodiment the generated physical properties are generated with all possible tissue compartment distributions.

In accordance with one embodiment the two or more physical properties comprises one or many of T1, T2 R1, R2 and PD.

In accordance with one embodiment relating observed physical properties of the generated maps to the physical properties generated using the simulation model is performed using look-up table.

In accordance with one embodiment at least one myelin sub-map from the myelin fraction map is generated.

In accordance with one embodiment the myelin sub(s) comprises one or many of a myelin water map, a myelin semi-solids map, a intra- and extracellular (interstitial) water map, a non-myelin semi-solids map, a free water map, a total water content map, a myelin water fraction map, an edema map, a total myelin content of the brain map and a relative myelin fraction of the brain map.

In accordance with one embodiment the interacting tissue compartments comprises one or many of a myelin fraction compartment, a cellular fraction compartment, a free water fraction compartment, a myelin water compartment, a myelin semi-solids compartment, a intercellular and interstitial water, compartment and a non-myelin semi-solids compartment.

The invention also extends to a computerized imaging system arranged to perform the methods as described herein and also to a digital storage medium having stored thereon computer program instructions/software segments that when executed by a computer causes the computer to execute the methods as described herein.

In accordance with one exemplary embodiment the computerized imaging system comprises for generating a map of myelin tissue of a brain comprises a first imaging circuitry arranged to generate maps of two or more physical properties of the brain, and a simulation model comprising at least two interacting tissue compartments. The system further comprises a controller arranged to generate physical properties using the simulation model as input, and a controller arranged to relate observed physical properties of the generated maps to the physical properties generated using the simulation model. A second imaging circuitry that can be the same as the first image circuitry is provided and arranged to generate a myelin fraction map of the brain using the relationship.

To enable imaging of myelin a controller unit/imaging circuitry for performing the above methods can be provided in a computer. The controller(s) and or imaging circuitry can be implemented using suitable hardware and or software. The hardware can comprise one or many processors that can be arranged to execute software stored in a readable storage media. The processor(s) can be implemented by a single dedicated processor, by a single shared processor, or by a plurality of individual processors, some of which may be shared or distributed. Moreover, a processor or may include, without limitation, digital signal processor (DSP) hardware, ASIC hardware, read only memory (ROM), random access memory (RAM), and/or other storage media.

Among the advantages of the methods described herein is that an absolute value of myelin fraction per unit volume can be obtained, which is useful in understanding MRI brain images. Also the value can be obtained based on a short MR acquisition. In addition derived from the myelin fraction also the myelin water, the myelin semi-solids, the intra- and extracellular (interstitial) water, the non-myelin semi-solids, the free water, the total water content, the myelin water fraction, edema, the total myelin content of the brain and the relative myelin fraction of the brain can be obtained.

BRIEF DESCRIPTION OF THE DRAWINGS

The present invention will now be described in more detail by way of non-limiting examples and with reference to the accompanying drawings, in which.

DETAILED DESCRIPTION

Figure 1:
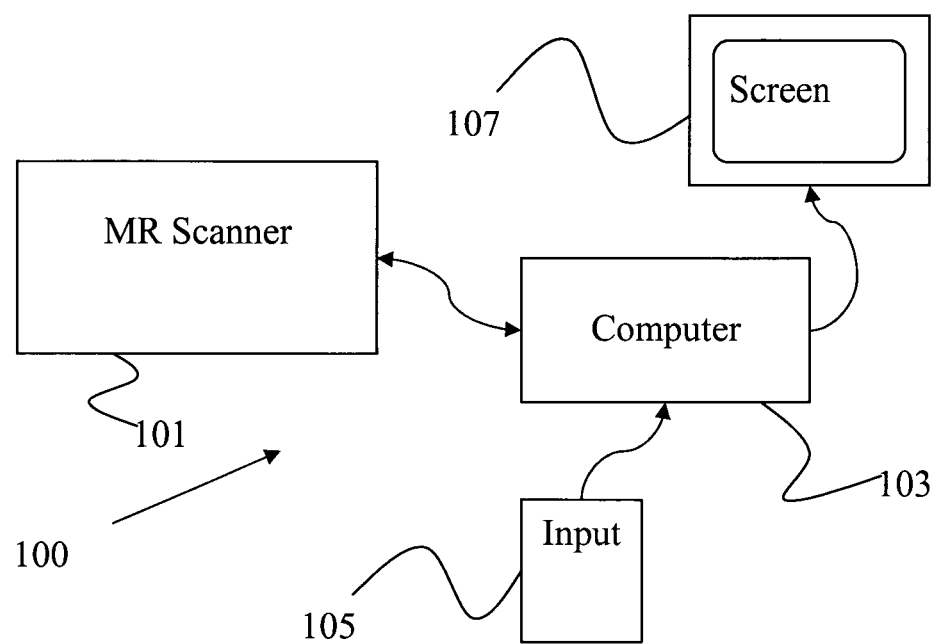
FIG. 1 is a schematic outline of an MR system

In FIG. 1 a general view of a setup of a MRI system 100 is depicted. The system 100 comprises a MR scanner 101. The MR scanner is operative to generate MRI data by means of scanning a living object. The MR scanner is further connected to a computer 103 for processing data generated by the scanner 101. The computer comprises a central processor unit coupled to a memory and a number of input and output ports for receiving and outputting data and information. The computer 103 receives input commands from one or several input devices generally represented by an input device 105. The input device may be one or many of a computer mouse, a keyboard, a track ball or any other input device. The computer 103 is further connected to a screen 107 for visualizing the processed scanner data as a contrast image. In particular the computer 103 can comprise controller unit(s)/imaging circuitry arranged to perform methods as described herein.

Figure 2:
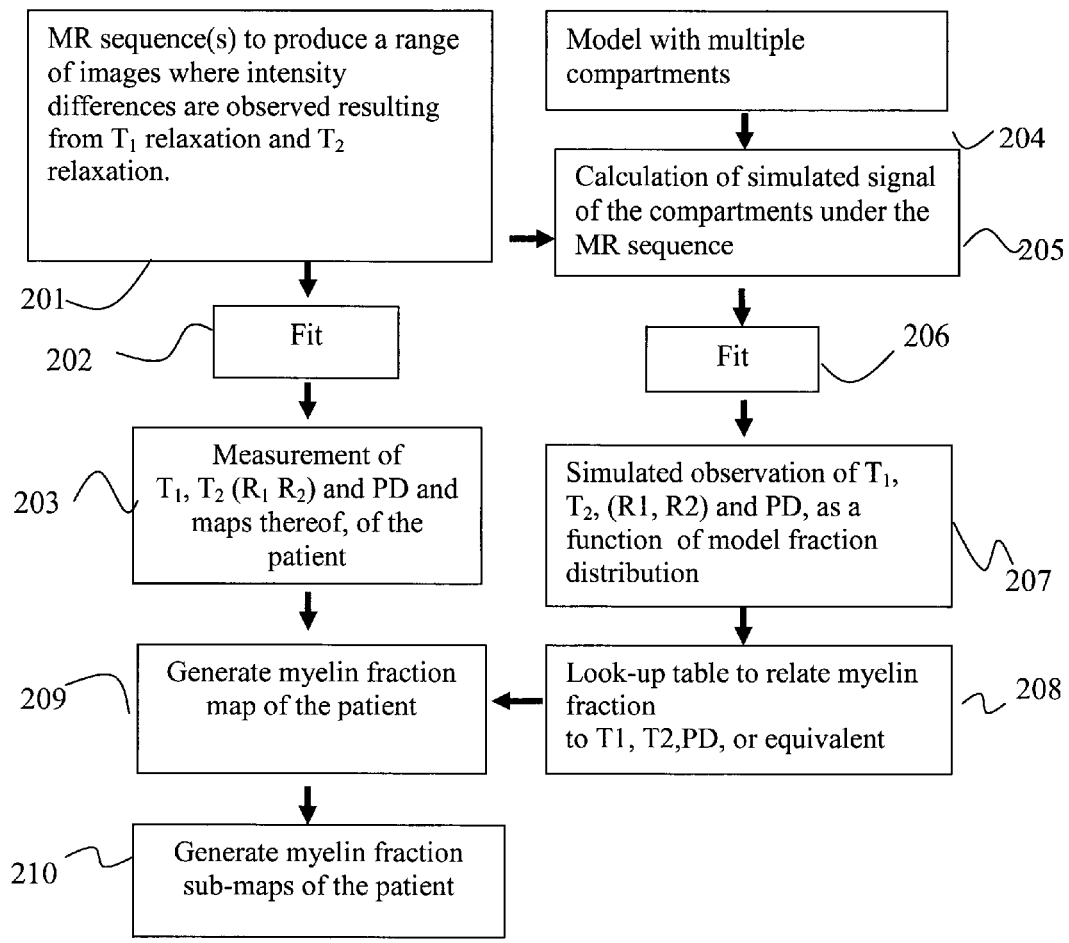
FIG. 2 is a flow chart illustrating some procedural steps performed when generating an MR image.

In FIG. 2, a flow chart illustrating steps performed when generating a myelin map. First, maps of two or more physical properties of the brain are generated. This can for example be performed using the steps 201-203 below.

Thus, in a step 201 one or several MR sequence(s) are generated resulting in a range of images where intensity differences are observed resulting from T1 relaxation and T2 relaxation of the tissues in the object, in this case the brain. This can be done by changing the scanner settings such as echo time TE, repetition time TR, the flip angle or the delay after a pre-pulse. A fit is performed in step 202, using these images, to calculate physical properties such as T1, T2, R1, R2 and PD (or equivalent), calculated as quantification maps of the brain in a step 203. See for example J. B. M. Warntjes, O. Dahlqvist Leinhard, J. West and P. Lundberg, Rapid Magnetic Resonance Quantification on the brain: Optimization for Clinical Usage, Magn Reson Med 60; 320-329 (2008).

A simulation model is designed in step 204 with multiple, interacting tissue compartments, as is further exemplified below in conjunction with FIG. 3. The number of tissue compartments can be any suitable number deemed appropriate for the simulation model. Next, in a step 205 the simulated signal intensity of these compartments under the influence of the MR sequence can be calculated. Using the simulated physical properties such as T1, T2 and PD, values are calculated as a function of tissue compartment distributions in a step 206. In accordance with one embodiment all possible tissue compartment distribution can be simulated. In particular the fit as used in step 202 can be used to provide simulations of the possible tissue compartment distributions (step 207).

These simulations can be used to generate a look-up table or descriptive functions in step 208 to relate any tissue distribution to the calculated physical property, such as T1, T2 and PD, observations. The look-up table or similar can then be used to generate a myelin fraction map of the brain of a patient based on the calculated physical properties such as T1, T2 and PD in a step 209. Based on the myelin fraction map generated in step 209, the related myelin sub-maps are calculated in step 210, such as a myelin water map, the myelin semi-solids map, the intra- and extracellular (interstitial) water map, the non-myelin semi-solids map, the free water map, the total water content map, the myelin water fraction map, the edema map, the total myelin content of the brain and the relative myelin fraction of the brain. The total myelin content is the sum of the myelin fractions per unit volume over the complete brain. Similarly, the relative myelin fraction of the brain can be derived from the fractions, where relative myelin fraction is the sum of the myelin fractions per unit volume over the complete brain divided by the volume of the brain.

Also in accordance with another embodiment, instead of performing the simulation and saving the result in a look-up table and then using the look up table to relate the different physical properties it is possible to make a curve fitting using the simulation model after the measurement. In such an embodiment the simulation would have to be performed every time the result was needed, but there would not be a need to use a look-up table.

Figure 3:
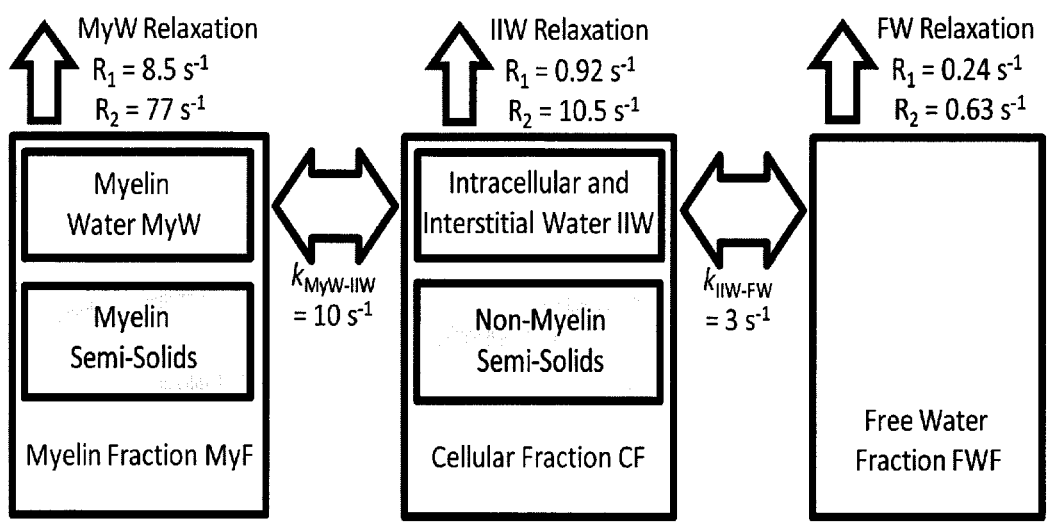
FIGS. 3-6 are plots and illustrations further illustrating a method to derive images of myelin and related quantities.

In FIG. 3 an example of a simulation model for the observed $R_1$, $R_2$ and PD of the brain is shown. Each acquisition voxel volume is partitioned into a myelin fraction (MyF), a cellular fraction (CF) and a free water fraction (FWF). The MyF compartment comprises of myelin water (MyW) and the myelin semi-solids (MSS). The CF compartment comprises of intracellular and interstitial water (IIW) and the non-myelin semi-solids (non-MSS). The free water fraction only consists of water. Each fraction has its own physical properties, expressed in R1, R2 and PD. Between MyF and the CF there is an interaction expressed as magnetization exchange rate $k_{MyF-cF}$ that couples the magnetization evolution of both fractions. Likewise there is a magnetization exchange rate $k_{CF-FWF}$ between CF and the FWF. The effective, observable R1, R2 and PD of the complete volume is the result of the behaviour of the coupled fractions. The relaxation rate values and fractional distributions are only indicative and serve as example values. The sum of all compartments makes up the complete image segment/image acquisition voxel.

All of the steps described in conjunction with FIG. 2 can be implemented in a computer by, for example but not limited to, executing suitable software program loaded into the computer on a digital storage media and causing the computer to execute the above steps. The method can also be implemented using a suitable computer, or hardware, comprising suitable image circuitry and controllers in combination with different models and memories, for example in the form of look-up tables.

It is further to be noted that the simulation model in FIG. 3 comprises three compartments. It is however to be understood that more (or fewer) compartments with interactions between them can be used. For example in FIG. 3, the myelin fraction compartment can be further sub-divided into myelin water MyW and myelin semi-solids. Also the cellular fraction compartment can be further sub-divided into intercellular and interstitial water, IIW, and non-myelin semi-solids with respective interaction.

Figure 4:
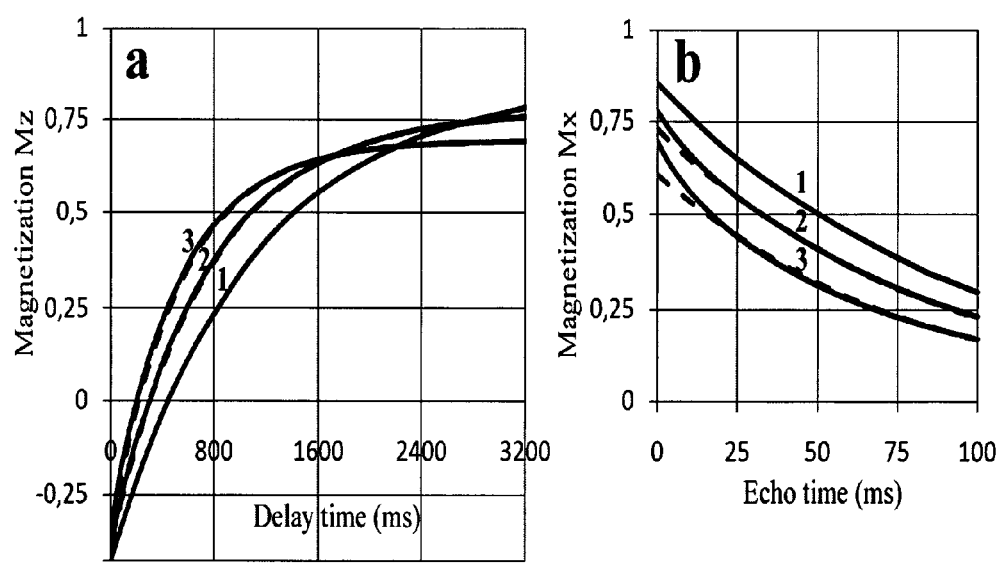

An example of a simulation model outcome is shown in FIG. 4. The fractional distribution is set to e.g. 30% myelin fraction, 70% cellular fraction and 0% free water fraction. The magnetization behavior over time is calculated resulting in signal intensity curves where R1, R2 and PD can be derived. In this example the result is R1=1.68 s$^{-1}$, R2=12.5 s$^{-1}$ and PD=64%. Hence a measurement of (R1, R2, PD)= (1.68, 12.5, 0.64) corresponds to (MyF, CF, FWF)=(0.3, 0.7, 0.0). This can be repeated for all possible fractional distributions to predict all potential measurement results.

Thus, in FIGS. 4a and 4b, simulation of the expected magnetization of three tissue fraction distributions using the rate values used in conjunction with FIG. 2 is depicted. In FIG. 4a the longitudinal magnetization A as a function of delay time after a 120 degrees RF saturation pulse. In FIG. 4b the transverse magnetization $M_x$ as a function of echo time after a 90 degrees RF excitation pulse. Shown in FIGS. 4a and 4b are the magnetization of 1. 100% CF, 2. 15% MyF and 85% CF and 3. 30% MyF and 70% CF. The FWF was zero in all three cases. The dashed lines are the mono-exponential fits on the corresponding signal intensity for $R_1$ and $R_2$. For $R_2$ the first 10 ms echo time is ignored to reflect experimental conditions. This leads, in general, to an underestimation of the calculated PD since the rapid decay at short echo times is missed experimentally. The estimated ($R_1$, $R_2$, PD) values of the three curves are (0.92, 10.5, 0.85), (1.26, 11.4, 0.75) and (1.68, 12.5, 0.64), respectively.

Figure 5:
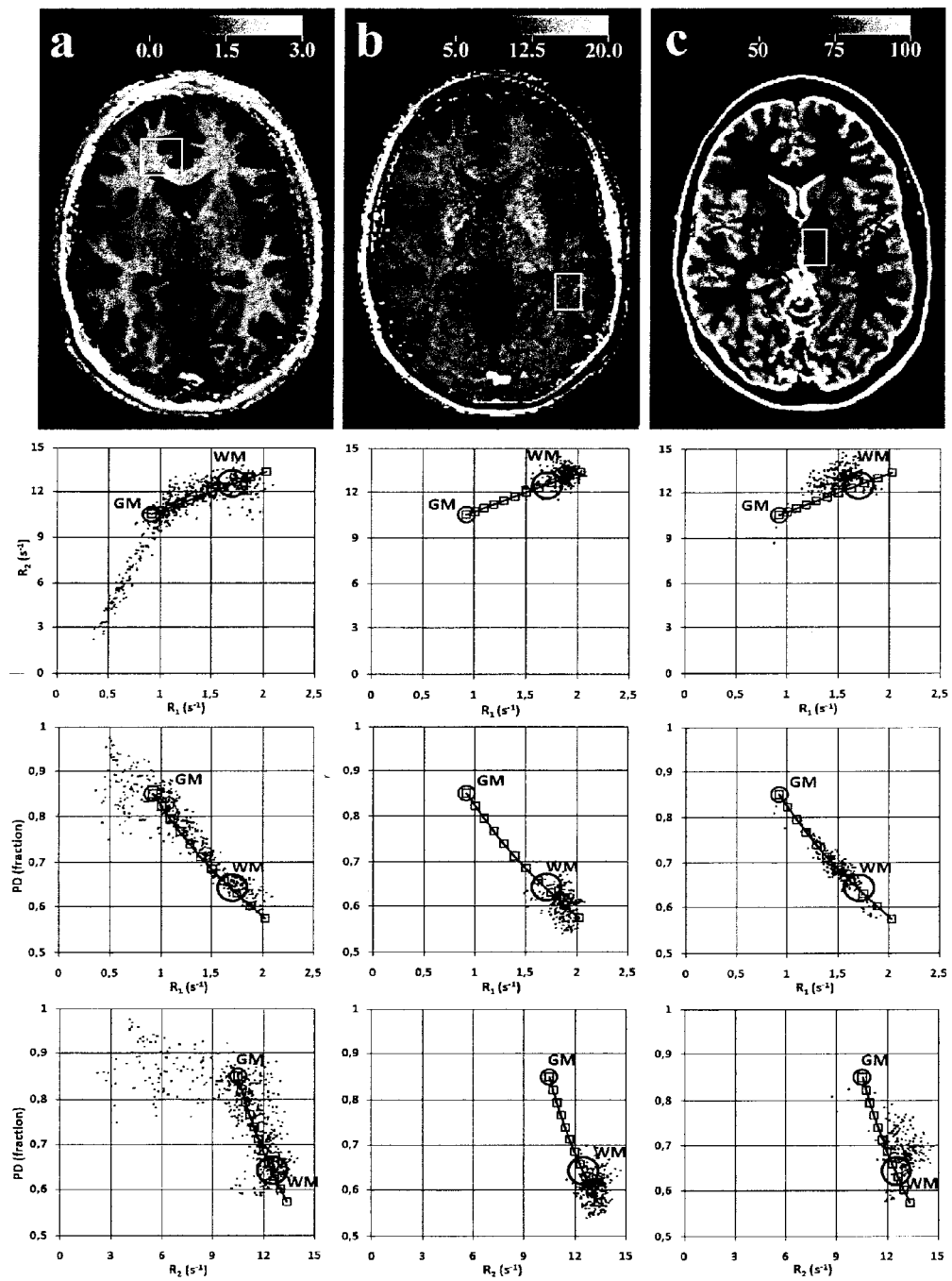

In FIG. 5 typical R1, R2 and PD maps are shown of the brain with regions of interest (ROI). The data inside the ROIs are plotted in the graphs below on the R1-R2, R1-PD and R2-PD projections of the R1-R2-PD space. The outcome of the simulation model where the myelin fraction ranges between 0-40% is added. The typical positions of grey matter (GM) and white matter (WM) are indicated by the circles.

Each point in the R1-R2-PD can be assigned a certain fraction distribution resulting in a translation of R1, R2 and PD into a specific distribution of myelin fraction, cellular fraction and free water fraction. In FIG. 5 a typical example of quantitative MRI data of a transversal slice of the brain of a healthy subject (female, 38 years) at a field strength of 1.5 T is depicted: a. $R_1$ relaxation rate on a scale 0-3 s$^{-1}$, b. $R_2$ relaxation rate on a scale 5-20 s$^{-1}$, c. Proton density on a scale 50-100% where 100% corresponds to pure water at 37° C. Three regions of interest are indicated where the $R_1$-$R_2$-PD data is plotted on the $R_1$-$R_2$, $R_1$-PD and $R_2$-PD projection planes below the images. The MyF/CF ratio is changed between 0/100% to 40/60% in steps of 4%, as indicated with the square markers. The mean GM and WM cluster positions are indicated with the circles. In the $R_1$ image the ROI is placed in an area with partial volume of GM, WM and CSF. The resulting data envelope has a typical bend at the GM position and data along the indicated line. In the $R_2$ plot the ROI is placed in an area with only WM and in the PD plot the ROI is placed at the thalamus.

Figure 6:
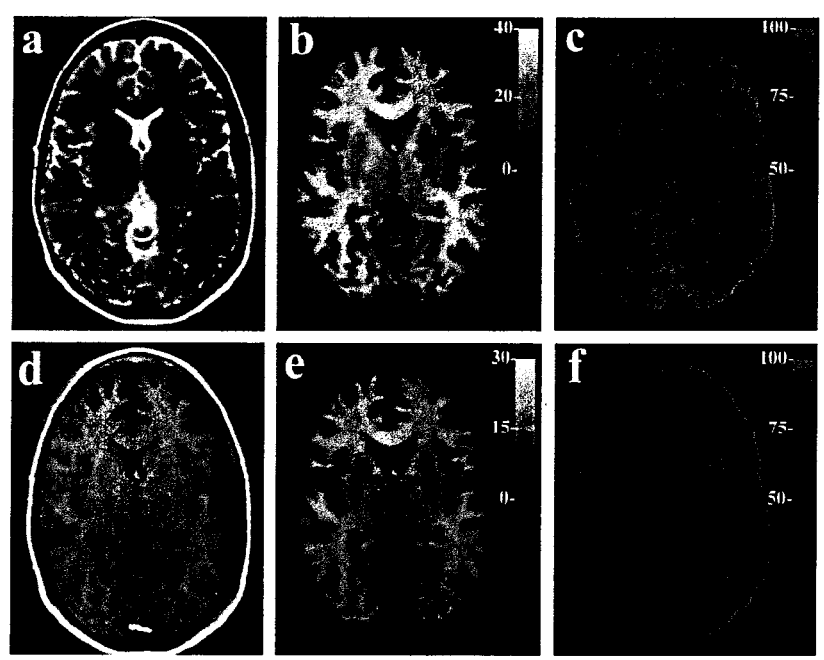

In FIG. 6 a number of fractions and derived quantities are shown of the same slice of FIG. 5 Myelin fraction (b), cellular fraction (c), myelin water fraction (e) and total water content (f). For comparison a conventional T2W (a) and a T1W (d) image are added. T2W image (a) of the slice displayed in FIG. 4 with the calculated myelin fraction on a scale 0-40% (b) and the cellular fraction, on a scale 50-100% (c). Also displayed is the T1W image of the slice (d) with the MWF (MyW/total water content), on a scale 0-30% (e) and the total water content on the slice (corresponding to MyW+ IIW, where the CSF is not masked) on a scale 50-100% (f). The red intracranial cavity outline is displayed in all images for visual guidance.

What is claimed is:

1. A computerized method of generating a myelin tissue fraction map of a brain in a displayable form, comprising:

generating at least one magnetic resonance (MR) sequence of the brain with an MR scanner, thereby producing a range of images having different signal intensities;

generating, in a computer based on using the range of images, a map of two or more observed physical properties of the brain, wherein a respective set of the two or more observed physical properties is determined for each voxel of the map; and the two or more physical properties include at least two of longitudinal relaxation time T1, transverse relaxation time T2, and proton density PD or at least two properties based on longitudinal relaxation time T1, transverse relaxation time T2, and proton density (PD);

forming, in the computer, a simulation model by:
partitioning each voxel into at least a myelin fraction, a cellular fraction, and a free water fraction, each of the myelin, cellular, and free water fractions having corresponding longitudinal relaxation rate (R1), a corresponding transversal relaxation rate (R2) and a corresponding PD, determining a first magnetic evolution coupling between the myelin fraction and the cellular fraction, and determining a second magnetic evolution coupling between the cellular fraction and the free water fraction, providing values for the myelin, cellular, and free water fractions, and generating values of longitudinal relaxation rate (R1), transversal relaxation rate (R2) and PD corresponding to the provided values of the myelin, cellular, and free water fractions based on the provided values and the first and second magnetic evolution couplings; and assigning, in the computer to each voxel of the map, at least a myelin tissue fraction by matching the voxels' observed R1, R2, and PD to a set of R1, R2, and PD generated by the simulation model, the myelin tissue fraction assigned corresponding to a myelin fraction used in the simulation model to generate the set of R1, R2, and PD, thereby generating the myelin tissue fraction map of the brain.

2. The method of claim 1, wherein the generating of values of R1, R2, and PD in the simulation model includes generating values of R1, R2, and PD for all possible tissue compartment distributions.

3. The method of claim 1, wherein matching the voxels' observed R1, R2, and PD to the set of R1, R2, and PD includes using a look-up table.

4. The method of claim 1, further comprising generating at least one myelin sub-map from the myelin tissue fraction map of the brain.

5. The method of claim 4, wherein the at least one myelin sub-map comprises at least one of a myelin water map, a myelin semi-solids map, an intra- and extra-cellular water map, a non-myelin semi-solids map, a free water map, a total water content map, a myelin water fraction map, an edema map, a total myelin content of the myelin fraction map, and a relative myelin fraction of the myelin fraction map.

6. A computerized imaging system for generating a myelin tissue fraction map of a brain in a displayable form, comprising:

a first imaging circuitry configured to generate, based on using a range of images produced from at least one magnetic resonance (MR) sequence, a map of at least two observed physical properties of the brain, wherein signal intensities of images are different; a respective set of the at least two observed physical properties is generated for each voxel of the map; and the at least two physical properties include at least one of longitudinal relaxation time T1, transverse relaxation time T2, and proton density PD or at least two physical properties based on longitudinal relaxation time T1, transverse relaxation time T2, and proton density;

a simulation model in the computerized imaging system, that is formed by:

partitioning each voxel into at least a myelin fraction, a cellular fraction, and a free water fraction, each of the myelin, cellular, and free water fractions having corresponding longitudinal relaxation rate (R1), a corresponding transversal relaxation rate (R2) and a corresponding PD, determining a first magnetic evolution coupling between the myelin fraction and the cellular fraction, and determining a second magnetic evolution coupling between the cellular fraction and the free water fraction, providing values for the myelin, cellular, and free water fractions, and generating values of longitudinal relaxation rate (R1), transversal relaxation rate (R2) and PD corresponding to the provided values of the myelin, cellular, and free water fractions based on the provided values and the first and second magnetic evolution couplings; and a second controller configured to match, for each voxel of the map, the voxels' observed R1, R2, and PD to a set of R1, R2, and PD generated by the simulation model; and a second imaging circuitry arranged to generate the displayable myelin tissue fraction map by assigning to each voxel of the map a myelin tissue fraction corresponding to the set of R1, R2, and PD that match the observed R1, R2, and PD.

7. The system of claim 6, wherein the generating of values of R1, R2, and PD in the simulation model includes generating values of R1, R2, and PD for all possible tissue compartment distributions.

8. The system of claim 6, further comprising a look-up table configured to match the voxels' observed R1, R2, and PD to the values of R1, R2, and PD generated in the simulation model.

9. The system of claim 6, wherein the system further comprises an imaging circuitry configured to generate at least one myelin sub-map from the myelin tissue fraction map of the brain.

10. The system of claim 9, wherein the at least one myelin sub-map comprises at least one of a myelin water map, a myelin semi-solids map, an intra- and extracellular water map, a non-myelin semi-solids map, a free water map, a total water content map, a myelin water fraction map, an edema map, a total myelin content of the myelin fraction map, and a relative myelin fraction of the myelin fraction map.

11. A non-transitory computer-readable medium encoded with computer-readable instructions that, when executed by a computer, cause the computer to perform a method comprising:

generating at least one magnetic resonance (MR) sequence of the brain with an MR scanner, thereby producing a range of images having different signal intensities;

generating, in a computer based on using the range of images, a map of two or more observed physical properties of the brain, wherein a respective set of the two or more observed physical properties is determined for each voxel of the map; and the two or more physical properties include at least two of longitudinal relaxation time T1, transverse relaxation time T2, and proton density PD or at least two properties based on longitudinal relaxation time T1, transverse relaxation time T2, and proton density PD;

forming, in the computer, a simulation model by:

partitioning each voxel into at least a myelin fraction, a cellular fraction, and a free water fraction, each of the myelin, cellular, and free water fractions having corresponding longitudinal relaxation rate (R1), a corresponding transversal relaxation rate (R2) and a corresponding PD, determining a first magnetic evolution coupling between the myelin fraction and the cellular fraction, and determining a second magnetic evolution coupling between the cellular fraction and the free water fraction, providing values for the myelin, cellular, and free water fractions, and generating values of longitudinal relaxation rate (R1), transversal relaxation rate (R2) and PD corresponding to the provided values of the myelin, cellular, and free water fractions based on the provided values and the first and second magnetic evolution couplings; and assigning, in the computer to each voxel of the map, at least a myelin tissue fraction by matching the voxels' observed R1, R2, and PD to a set of R1, R2, and PD generated by the simulation model, the myelin tissue fraction assigned corresponding to a myelin fraction used in the simulation model to generate the set of R1, R2, and PD, thereby generating a myelin tissue fraction map of the brain in a displayable form.

12. The non-transitory storage medium of claim 11, wherein the generating of values of R1, R2, and PD in the simulation model includes generating values of R1, R2, and PD for all possible tissue compartment distributions.

13. The non-transitory storage medium of claim 11, wherein matching the voxels' observed R1, R2, and PD to the set of R1, R2, and PD includes using a look-up table.

14. The non-transitory storage medium of claim 11, wherein the computer is further caused to perform generating at least one myelin sub-map from the myelin tissue fraction map of the brain.

15. The non-transitory storage medium of claim 14, wherein the at least one myelin sub-map comprises at least one of a myelin water map, a myelin semi-solids map, an intra- and extracellular water map, a non-myelin semi-solids map, a free water map, a total water content map, a myelin water fraction map, an edema map, a total myelin content of the myelin fraction map, and a relative myelin fraction of the myelin fraction map.

16. The method of claim 1, further comprising varying at least one MR scanner setting to generate the images having different signal intensities.

17. The system of claim 6, further comprising a scanner configured to generate the at least one magnetic resonance (MR) sequence.

18. The system of claim 17, wherein the scanner has at least one variable setting for generating the images having different signal intensities.

19. The non-transitory computer-readable medium of claim 11, further comprising causing the computer to vary at least one MR scanner setting to generate the images having different signal intensities.

* * * * *